United States Patent [19]

Gilbert

[11] Patent Number: 4,875,372

[45] Date of Patent: Oct. 24, 1989

[54] ECHO CANCELLATION SYSTEM

[75] Inventor: Dennis H. Gilbert, Renton, Wash.

[73] Assignee: The Boeing Company, Seattle, Wash.

[21] Appl. No.: 189,898

[22] Filed: May 3, 1988

[51] Int. Cl.⁴ .............................................. G01N 29/04
[52] U.S. Cl. .......................................... 73/614; 73/615
[58] Field of Search ................ 73/627, 628, 629, 630, 73/631, 610, 614, 611, 615, 600, 602, 613; 328/165; 364/507

[56] References Cited

U.S. PATENT DOCUMENTS

| 4,041,774 | 8/1977 | Morris et al. | 73/610 |
| 4,098,130 | 7/1978 | Coffey et al. | 73/610 |
| 4,545,251 | 10/1985 | Uchida et al. | 73/631 |

Primary Examiner—John Chapman
Assistant Examiner—Robert P. Bell
Attorney, Agent, or Firm—Conrad O. Gardner; B. A. Donahue

[57] ABSTRACT

An ultrasonic inspection system for composite materials capable of detecting flaws near the surface of the inspected part which flaws are normally masked by strong reflections from the part surface. An electronic signal representative of the strong surface echo is stored in memory and subtracted in a differential amplifier from the entire test piece echo representative signal in time relationship which effects cancellation of the signal representative of the strong surface echo thereby allowing weaker echo representative signals from defects near the surface to the detected.

2 Claims, 2 Drawing Sheets

ECHO CANCELLATION SYSTEM

BACKGROUND OF THE INVENTION

This invention relates to an echo cancellation system, and more particularly, to an echo cancellation system for use in pulse echo ultrasonic inspection systems.

A significant limitation of pulse echo ultrasonic inspection systems is the inability to detect flaws or foreign objects near the surface of a part.

In pulse echo inspection systems, an echo is received from the front surface of the test item. This is due to the acoustic impedance mismatch at the delay line/part interface. The front surface echo effectively masks any echoes from flaws or foreign objects very close to the surface. The presence of a piece of backing paper between the first and second plies in a graphite laminate is virtually undetectable. The usual method for overcoming this problem is to use a higher frequency transducer. This provides better near surface resolution by reducing the time duration of the interface echo. There are two main drawbacks to this method. First, since ultrasonic attenuation increases with frequency, echoes from defects deep in a part will be too weak for detection. Secondly, higher frequency transducers are more sensitive to porosity and other fine structure properties which might overshadow more important flaws like delaminations. Another method of detecting near surface flaws is to use TTU (through-transmission technique). Unfortunately, TTU is not sensitive enough to detect some types of foreign materials and it does not provide any depth information.

Prior patent literature discloses signal canceling circuits as seen for example in U.S. Pat. No. 4,093,923. In U.S. Pat. No. 4,093,923 a reference signal is stored in memory and subtracted from a real signal. In U.S. Pat. No. 4,093,923 the signal cancelling circuit is used to cancel constant, low frequency (60 Hz) background noise, whereas the present echo cancellation system is utilized to eliminate a complex high frequency signal. The signal cancelling circuit of U.S. Pat. No. 4,093,923 requires a constant phase signal in contrast to the present system where the signal is independent of phase. In the present echo cancellation system, the reference signal is clocked out of memory when the front surface echo is detected so any changes in the transducer part surface distance does not effect the echo cancellation. A further distinct difference from the prior art is that the present echo cancellation device uses a high speed analog to digital converter and digital memory whereas the prior art signal cancelling circuit of U.S. Pat. No. 4,093,923 uses sample and hold circuitry to acquire and store the reference waveform. The sample and hold circuit of the aforementioned prior art patent reference is suitable for a constant 60 Hz sine wave where about ten samples would be more than adequate, but in the case of a complex waveform requiring several hundred or more samples, the prior system would be impractical due to complexity and cost. By using an A to D converter and digital memory, the present echo cancellation system can store several thousand samples at minimal cost.

SUMMARY OF THE INVENTION

It is accordingly an object of the present invention to provide an ultrasonic inspection system for composite materials which utilizes an echo cancellation system capable of detecting flaws near the surface of the inspected part which flaws are normally masked by strong reflections from the part surface. With the transducer positioned over a defect free region of the test item, the front surface echo is digitized and stored in memory. During the inspection, the signal is clocked out of memory and subtracted from the apparent front surface echo in real time.

BRIEF DESCRIPTION OF THE DRAWINGS

The present invention will be readily apparent from the embodiment illustrated in the accompanying drawings in which.

DESCRIPTION OF THE PREFERRED EMBODIMENTS

Figure 1A:
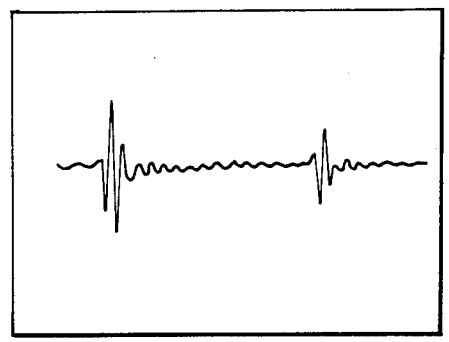
FIGS. 1A and B show pulse echo signals with front and back surface echoes from 0.4 inch thick graphite epoxy laminate, FIG. 1A showing a defect free region and FIG. 1B showing backing paper between the first and second plies.
Figure 1B:
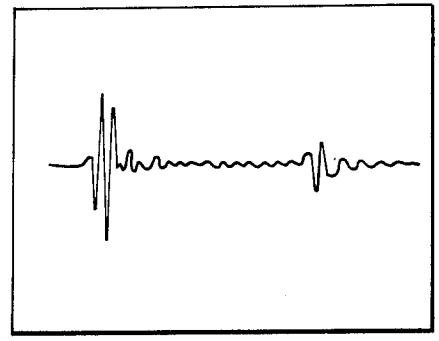

Referring now to the drawings, it can be seen from FIGS. 1A and B which represent the defect free region and backing paper between first and second plies respectively at the presence of a piece of backing paper between the first and second plies in a graphite laminate is virtually undetectable in prior systems. This can be contrasted as hereinafter described with FIGS. 2A and B respectively which are illustrative of the present echo cancellation system in operation.

Figure 2A:
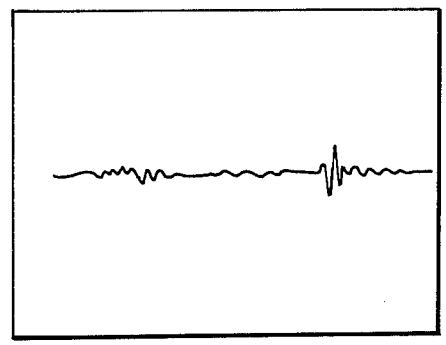
FIGS. 2A and B are illustrative of the same back pulse echo signals utilizing the present echo cancellation system.
Figure 2B:
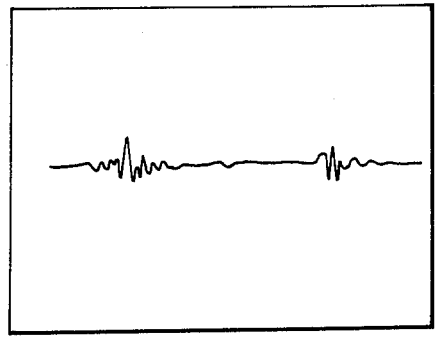

The apparent front surface echo is a superposition of the actual front surface echo and echoes from flaws or foreign objects very close to the surface, therefore, if the contribution from the front surface can be subtracted from the apparent echo, then what remains are just the contributions from defects near the surface. These defects would then be detectable. FIGS. 2A and B show the present echo cancellation system in operation and can be contrasted to the prior corresponding FIGS. 1A and B. FIG. 2A shows a defect free region and FIG. 2B shows the backing paper between first and second plies. The effectiveness of the present echo cancellation system is readily recognized for its effectiveness in cancelling the front surface echo, and hence improving the near surface resolution.

Figure 3A:
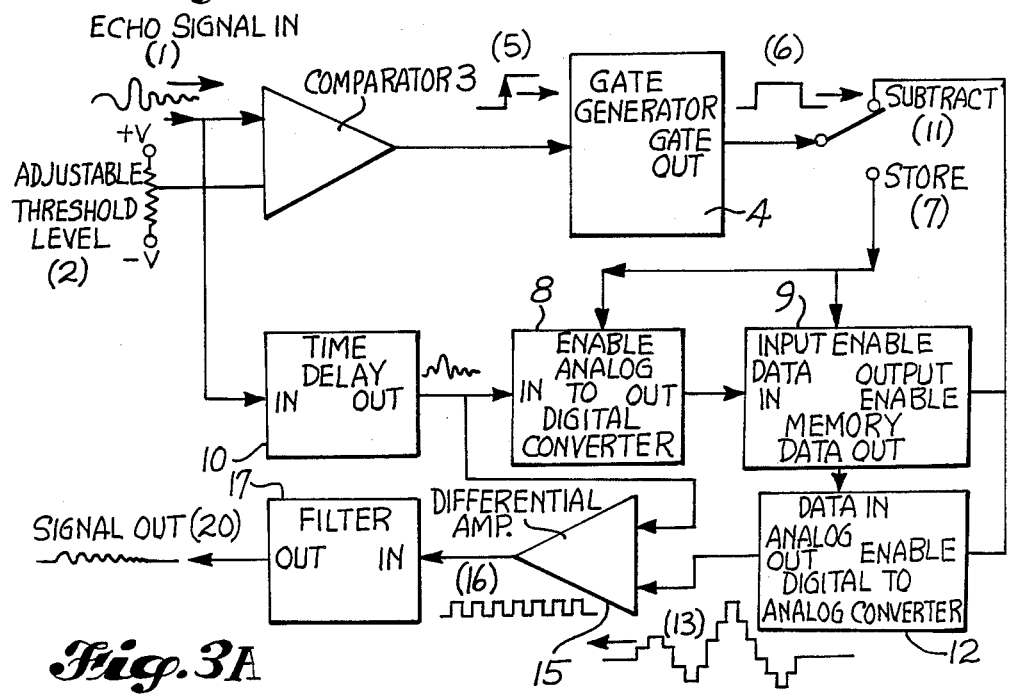
FIG. 3 is a functional schematic diagram of the present echo cancellation system; and, FIG. 3B is a detailed timing diagram showing the corresponding signals of FIG. 3 for increased clarity.
Figure 3B:
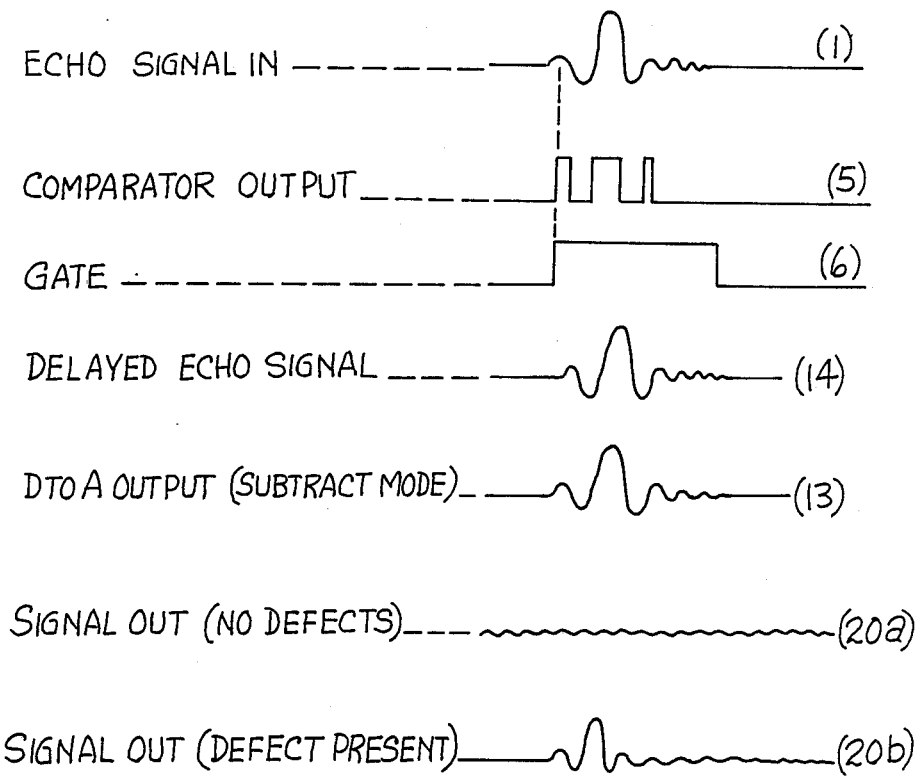

Turning now to FIG. 3A and the functional block schematic diagram of the present echo cancellation system, it can be seen that when an incoming signal 1 exceeds the threshold level 2, the comparator circuit 3 output changes to a TTL high state. Gate generator circuit 4 is triggered by the rising edge of wave shape 5 (shown in more detail as the comparator output 5 in FIG. 3B) and produces a TTL gate signal 6. In the store mode at circuit path 7, gate signal 6 enables analog to digital converter circuit 8 and memory circuit 9. Incoming echo signal 1 is delayed by a delay line 10, converted to digital signal format by A to D converter circuit 8, and stored in memory 9. Time delay provided by delay line 10 allows the entire waveform to be stored in memory. Without this feature, only the portion occurring after detection would be stored. In the subtract mode with the switch at circuit path 11, gate signal 6 enables memory 9 and digital to analog converter 12. The data is clocked out of memory 9 and converted to an analog signal 13 (shown in more detail in FIG. 3B) by the D to A converter 12. Analog signal 13 and the delayed incoming analog signal 14 are coupled to differential amplifier 15. Difference signal 16 from differential amplifier circuit 15 is coupled through filter circuit 17 which provides removal of artifacts due to the sampling clock (not shown). The store operation is performed while the ultrasonic probe generating the echo signal in (1) is positioned over a defect free region of the inspection item. The subtract mode (utilizing switching means through circuit path 11) is active during the actual inspection. In FIG. 3B the signal 20A denotes an output signal when there are no defects and the signal output 20B denotes the signal output when a defect is present.

The present system has provided a dramatic improvement in tests in the near surface resolution of a water jet scanner. The present echo cancellation system would appear to be more effective for inspection systems that have fixed delay lines (e.g. bubbler shoes, contact probes, etc.). In addition to the front surface echo, the present echo cancellation system can be utilized to cancel any unwanted steady signals such as transducer or delay line artifacts. The development and implementation of the present technique is made possible by the present high speed data conversion and memory devices. While a preferred embodiment has been shown in FIG. 3 in block diagram schematic form, it should become apparent to those skilled in the art that the present echo cancellation system could be used with any pulse echo inspection system. A particular advantage discovered in testing is the ability to detect flaws within the first two plies in graphite laminate, such being made possible with the present system resolution. Other uses and adaptations of the present echo cancellation system will become apparent to those skilled in the art.

What is claimed is:

1. In an ultrasonic inspection system, the method of detecting flaws near the surface of an inspected part including the steps of:
    storing in memory, a signal representative of a surface echo, and then,
    subtracting in a differential amplifier the signal representative of said surface echo from a signal representative of the inspected part thereby effecting cancellation of said signal representative of a surface echo and enabling detection of weaker signals representative of echoes from defects near the surface of the inspected part to be detected.

2. An echo cancellation system comprising in combination:
    a compactor circuit;
    gate generation circuit means connected to said compactor circuit for generating an enabling signal as a function of the output of the comparator circuit;
    analog to digital converter circuit means connected to a memory circuit for converting the echo signal to digital data for storage in memory;
    switching means connected between said gate generator circuit means and said analog to digital converter and said memory circuit for selecting either the memory input or the memory output;
    a time delay circuit coupled between said comparator circuit and said analog to digital converter for delaying the echo signal;
    a digital to analog converter connected to said memory circuit for converting the previously stored digital data to an analog signal;
    a filter circuit for provided an output signal; and
    a differential amplifier circuit coupled between said further digital to analog converter and said filter circuit for subtracting the recalled signal from the current echo signal.

* * * * *